(12) United States Patent
Desprez et al.

(10) Patent No.: US 7,427,491 B2
(45) Date of Patent: Sep. 23, 2008

(54) NANOPARTICLES FOR OPTICAL SENSORS

(75) Inventors: Valerie Desprez, Heidelberg (DE); Norbert Oranth, Freilberg (DE); Jurgen Spinke, Lorsch (DE); James Kenneth Tusa, Roswell, GA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 312 days.

(21) Appl. No.: 10/888,392

(22) Filed: Jul. 9, 2004

(65) Prior Publication Data
US 2005/0019849 A1    Jan. 27, 2005

(30) Foreign Application Priority Data
Jul. 10, 2003 (EP) .................. 03015781

(51) Int. Cl.
*C12Q 1/54* (2006.01)
(52) U.S. Cl. .................. 435/14; 204/403.04
(58) Field of Classification Search .......... 435/14; 204/403.04; 436/518, 528
See application file for complete search history.

(56) References Cited

U.S. PATENT DOCUMENTS

| 5,272,087 | A | * | 12/1993 | El Murr et al. | 204/403.04 |
| 6,107,083 | A | * | 8/2000 | Collins et al. | 435/288.7 |
| 6,238,930 | B1 | * | 5/2001 | Spichiger-Keller et al. | 436/518 |
| 6,764,581 | B1 | * | 7/2004 | Forrow et al. | 204/403.14 |
| 2003/0138842 | A1 | * | 7/2003 | Seul et al. | 435/7.1 |
| 2005/0037374 | A1 | * | 2/2005 | Melker et al. | 435/6 |

FOREIGN PATENT DOCUMENTS

WO    WO99/32662    7/1999

OTHER PUBLICATIONS

Neubauer A. et al. Fibre Optic Glucose Biosensor Using Enzyme Membranes with 2-D Crystalline Structure. Biosensors & Bioelectronics 11(3)317-325, 1996.*
Wikipedia definition of Nanoparticle, Jan. 30, 2008.*

* cited by examiner

*Primary Examiner*—Ralph Gitomer
(74) *Attorney, Agent, or Firm*—Dinsmore & Shohl LLP

(57) ABSTRACT

The present invention concerns a polymer layer for a sensor, wherein the polymer layer has nanoparticles embedded therein which impart to the polymer layer recognizing properties as well as transducer properties, a sensor comprising such layer and the use of the sensor for detecting and/or quantifying a target analyte.

22 Claims, 2 Drawing Sheets

*A: one population of nanoparticles*

Nanoparticles doped with a luminescent dye and conjugated with an oxidative enzyme

*B: two populations of nanoparticles*

Nanoparticles doped with a luminescent dye

Nanoparticles conjugated with an oxidative enzyme

NANOPARTICLES FOR OPTICAL SENSORS

BACKGROUND OF THE INVENTION

The present invention concerns a polymer layer for a sensor, wherein the polymer layer has nanoparticles embedded therein which impart to the polymer layer recognizing properties as well as transducer properties, a sensor comprising such layer, and the use of the sensor for detecting and/or quantifying a target analyte.

Various sensors for determining substances of interest in a qualitative and quantitative manner have been described to date. In particular, in the fields of environmental and food technology, medicine, and biotechnology the development of precise analytical means and methods is of great interest. For example, enzyme-based sensors with electrochemical or optical transduction are widely used to determine analytes in the blood and in other body liquids.

Generally, classical sensors consist of a multilayer structure. For example, U.S. Pat. No. 6,107,083 describes an optical enzyme-based sensor with a multilayer structure which comprises, in the sequence of layers: (a) an oxygen-sensitive layer containing a luminescent dye in a light-transmissive, oxygen-permeable matrix, (b) an enzymatic layer containing an oxidative enzyme in a hydratable and oxygen-permeable matrix, and (c) a rapidly hydrating gas-permeable cover layer disposed over the enzymatic layer.

Major drawbacks of such multilayer-structured sensors are the complex buildup of the sensors involving problems with the coating compatibility of the multiple layers, the limited density of functional elements available on a planar surface, and the difficulty in controlling precisely the thickness of each layer in order to maintain reproducible diffusion processes. These processes are accompanied by unsatisfactory sensor responses and reduced signal yields.

In U.S. Pat. No. 6,238,930 B1 a different approach for a layer structure for the determination of a substance has been made by forming a micellar recognition system from two non-miscible phases, a surface-active substance and a recognition component, and by incorporating this system into a layer. The substance of interest is then detected by the interaction with the recognition component and a transducing step both occurring in the layer. The construction of the layer structure according to U.S. Pat. No. 6,238,930 B1 is complex and due to the requirement of forming appropriate micelles, the flexibility and field of application of such systems is limited. Compared to the classical multilayer-structured sensors no significant simplification could be achieved.

SUMMARY OF THE INVENTION

It is against the above background that the present invention provides certain unobvious advantages and advancements over the prior art. In particular, the inventors have recognized a need for improvements in nanoparticles for optical sensors. Although the present invention is not limited to specific advantages or functionality, it is noted that the invention provides a sensor with simplified and reproducible sensor design which allows for the precise determination of an analyte of interest.

The problem underlying the present invention is solved by a sensor comprising a polymer layer having recognizing and transducer properties, wherein these properties are provided by a recognizing component and a transducer contained in one or more nanoparticles embedded in the polymer layer.

In accordance with one embodiment of the present invention, wherein the recognizing component and the transducer are provided in one single layer, the number of layers in the sensor are reduced, leading to a simplified sensor production. Moreover, by combining the recognizing component and the transducer in close vicinity in a unique layer, fast sensor responses can be achieved and the efficiency of the sensor is less dependent on the layer thickness, resulting in better coating reproducibility. In particular, by providing nanoparticles which impart to the layer recognizing and transducer properties the sensor system can be conveniently adjusted to different sensor applications by varying the constituents and design of the nanoparticles. For example, the size, density, and arrangement of components can be varied. By that means, for example, it is possible to adjust the total amount of recognizing component or transducer in the polymer layer. In addition thereto, the use of functionalized nanoparticles in the polymer layer according to the present invention allows for adjustment of the sensitivity and dynamic range by changing the density of nanoparticles in the polymer layer. A further advantage of the sensor according to the present invention is that it is suitable for performing multiple measurements due to easy regeneration of the polymer layer.

The improved sensor according to the present invention is suitable for use in the fields of pharmaceutics, medicine, biotechnology, environmental and food technology, and drinking and waste water control. The sensor according to the invention, therefore, is brought together with a sample containing a substance to be detected, which leads to an interaction between the analyte and the recognizing component in the polymer layer. The interaction between the recognizing component and an analyte results in a product or a change in the conditions in the polymer layer. In the following description this interaction will be termed the "recognizing step." In close contact to the recognizing component the transducer is provided which consists of a component which is sensitive to a product or change in conditions resulting from the recognizing step. "Sensitivity" to the product or the change in conditions means that the transducer properties are changed by the influence of the product or the different ambient conditions, wherein the change in properties of the transducer can be detected.

Sensors based on the reaction of an oxidative enzyme for the detection of an oxidizable substance are particularly useful. In the enzymatic oxidation, oxygen in the environment of the enzyme is consumed, leading to a change in the oxygen concentration in the polymer layer which is directly connected with the amount of analyte in the sample. The change of the oxygen concentration can be made visible, for example, by using an oxygen-sensitive luminescent dye. By means of such dye the amount of analyte in the sample can be detected by measuring the change in the luminescence of the dye. In general, luminescence is quenched by oxygen, i.e., due to the consumption of oxygen, the enzymatic reaction leads to a stronger luminescence and the luminescence intensity change can be detected as a function of the amount of analyte in the sample.

The combination of recognizing and transducer properties in one single polymer layer in the sensor according to the present invention is realized by embedding functionalized nanoparticles into the polymer layer. Two types of functionalized nanoparticles can be used—1) particles comprising a recognizing component and a transducer, and 2) nanoparticles each comprising only one of the two components. These nanoparticles can be combined as desired, but must be chosen such that the polymer layer exhibits recognizing as well as transducer properties.

In a particular embodiment of the present invention, the polymer layer of the sensor has embedded therein first nanoparticles comprising a recognizing component and second nanoparticles comprising a transducer.

In another embodiment of the present invention, the polymer layer of the sensor has embedded therein nanoparticles comprising both a recognizing component and a transducer.

According to the present invention, the recognizing component is a chemical or biological substance which is capable of selectively interacting with an analyte in a recognizing step. Through this interaction the analyte can be detected and/or quantified. For example, the recognizing step is a reaction or coupling between the recognizing component and the analyte, leading to a detectable consumption of a substance, the formation of a detectable product, or to a detectable change of the ambient conditions.

Typically, the recognizing component is a bioactive component or living cells or bacteria. In particular, the bioactive component can be selected from the group consisting of enzymes, synthetic and gene-manipulated enzymes, antibodies, peptides, carbohydrates, lectins, lipids, and mixtures thereof. More typically, the bioactive component is an enzyme which can be selected from hydrolases, proteases and oxidases, depending on the substance to be detected. Oxidative enzymes are particularly suitable. For example, analytes which are enzyme-oxidizable such as glucose, cholesterol, lactate or sarcosine can be detected by using oxidative enzymes. The oxidative enzyme may be selected from the group consisting of glucose oxidase, cholesterol oxidase, lactate oxidase, sarcosine oxidase and mixtures thereof.

According to the present invention, the recognizing component can also consist of several chemical substances and/or biological substances, leading to a cascade recognizing system. This is particularly useful when the analyte of interest does not directly result in a detectable and quantifiable signal, respectively, by interaction with the recognizing component. Here, a second or further recognizing component reacts or interacts with the product of one of the foregoing recognizing steps to result in an appropriate product or change in the ambient conditions and to produce a signal.

The transducer according to the present invention consists of a component which is sensitive to a component of the recognizing step or to a change of the ambient conditions caused by this step. It can be an optical or electrochemical transducer, i.e., the resulting measurement variable is an optical signal and an electrical signal, respectively.

An optical transducer consists of a component which is capable of changing its spectral properties in dependence on the change of the ambient conditions caused by the recognizing step. The properties may be transformed by change of the pH, the presence of specific ions or molecules, oxidizing agents or reducing agents. For example, a change in intensity of the radiation emitted from the optical transducer can be influenced by a compound consumed or produced in the recognizing step and can be correlated with the presence and/or amount of the substance of interest. Such a change in intensity can be due to quenching of the emission, for example, by oxygen. Either by detecting a decrease or increase in luminescence intensity—depending on whether the recognizing step produces or consumes oxygen—information about the type and/or amount of analyte can be achieved. Generally, the quenching of emitted radiation, i.e., the presence of oxygen, leads to a decrease, while an increase is detected when oxygen is consumed. Further, the optical transducer can also consist of a substance which at first does not produce an optical signal but which is transformed by a product or by means of a change of the ambient conditions resulting from the recognizing step to produce an optical signal.

An electrochemical transducer, for example, reacts to a change of the current, potential or conductivity caused by the recognizing step.

In still another typical embodiment of the present invention, the transducer in the sensor is an optical transducer. Typically, the optical transducer consists of a dye which is sensitive to a component which is consumed or formed in the recognizing step. More typical is the use of a luminescent dye. Suitable dyes for use in the sensor of the present invention are selected from the group consisting of ruthenium(II), osmium (II), iridium(III), rhodium(III) and chromium(III) ions complexed with 2,2'-bipyridine, 1,10-phenanthroline, 4,7-diphenyl-1,10-phenanthroline, 4,7-dimethyl-1,10-phenanthroline, 4,7-disulfonated-diphenyl-1,10-phenanthroline, 5-bromo-1,10-phenanthroline, 5-chloro-1,10-phenathroline, 2,2'-bi-2-thiazoline, 2,2'-dithiazole, $VO^{2+}$, $Cu^{2+}$, $Zn^{2+}$, $Pt^{2+}$, and $Pd^{2+}$ complexed with porphyrin, chlorine, phthalocyanine, and mixtures thereof. In a typical embodiment, the luminescent dye is [Ru(diphenylphenantroline)3], octaethyl-Pt-porphyrin, octaethyl-Pt-porphyrin ketone, tetrabenzo-Pt-porphyrin, tetraphenyl-Pt-porphyrinmeso-tetraphenyl-tetrabenzo-Pt-porphyrin, tetracyclohexenyl-Pt-porphyrin, octaethyl-Pt-chlorine, tetraphenyl-Pt-chlorine, or a mixture thereof.

Further possible transducers, for example, contain indicators such as redox indicators which lead to an optical signal by the oxidation/reduction of the indicator, pH indicators responding to a change of the proton concentration and ionophores or other suitable chelating agents which form optically detectable chelates or complexes with ions and/or molecules formed in the recognizing step.

The nanoparticles comprising the recognizing component and/or the transducer typically are solid or semi-solid particles. More typical is the use of solid materials such as solid polymeric materials. The material of the solid or semi-solid particles generally may be selected from any inorganic or organic synthetic or natural material. Typically, the nanoparticles are made from polymeric materials or semiconductor materials (e.g., so-called quantum dots). Examples of suitable inorganic materials are $SiO_2$, $BaSO_4$, glass, etc. Organic materials may be selected from synthetic and natural polymers. Examples of natural polymers are alginates, cellulose or cellulose derivatives.

Specific examples of suitable polymers are polyolefins, vinyl polymers, polyamides, polyesters, polyacetals, polycarbonates, polyurethanes, polysiloxanes, and copolymers, and mixtures thereof. In particular, the nanoparticles can be made of polystyrene, poly(tert-butylstyrene), polyethylene, polypropylene, polybutene, polyisobutene, and copolymers, and mixtures thereof.

With oxidase enzymes as the recognizing component, the nanoparticles are typically made from polymers or co-polymers having a high oxygen permeability. Specific examples of suitable polymers are silicone, polybutadiene, and poly-(tert-butyl styrene).

The nanoparticles may comprise components to modify physical properties (e.g., density, reflective index) and the properties of active components. The size of the nanoparticles can vary from about 10 to about 500 nm of mean particle diameter. Typically, the mean diameter of the nanoparticles is about 30 to about 300 nm, more typically about 100 to about 200 nm. The size of the particles, for example, depends on the amount of active components to be incorporated in the nanoparticle or on the desired density of active components in the nanoparticles.

The recognizing component and/or the transducer is entrapped within, conjugated to, or attached to the nanoparticles or the nanoparticle material, respectively. For example, the recognizing component and/or the transducer are entrapped within the nanoparticle, i.e., they are not covalently bound to the nanoparticle material, but only held therein by physical entrapment. In particular, the active components are homogeneously distributed therein. It is also possible to conjugate the recognizing component and/or the transducer to the nanoparticle material at the surface of the nanoparticle and/or inside the nanoparticle. Conjugation is due to intermolecular forces such as electrostatic interaction, induction forces, and hydrogen bondings or ionic bonding. It is further possible to attach, i.e., covalently bind, the components onto the surface of the nanoparticles and/or to the nanoparticle material within the nanoparticles.

In yet another embodiment of the present invention, the transducer is entrapped within the nanoparticle and the recognizing component is covalently attached to the surface of the nanoparticle.

In yet still another embodiment of the present invention, the nanoparticle comprises both the transducer and the recognizing component, wherein the transducer is entrapped within the nanoparticle and the recognizing component is covalently attached to the surface of the nanoparticle.

In the sensor according to the present invention, the nanoparticles as described above are embedded in a polymer layer to impart to the layer recognizing as well as transducer properties. Embedment is accomplished by physical entrapment and/or covalent linking and/or conjugation of the nanoparticles to the polymer layer. Typically, the nanoparticles are dispersed in the polymer layer and are held therein by physical entrapment.

The nanoparticles can be homogeneously distributed in the polymer layer or it may be desired to have different densities of nanoparticles within the polymer layer. For example, it may be typical to have more nanoparticles near the contacting surface of the sensor than inside or at the other end of the layer.

In general, the polymer layers can be made from any inorganic or organic natural or synthetic polymer, wherein it is typical that the polymer is rapidly hydratable. Further, it may be typical that the polymer layer is oxygen-permeable, in particular, if oxygen is involved in the transducing step.

Examples of suitable polymers for the polymer layer in the sensor according to the present invention typically are selected from the group consisting of polyolefins, vinyl polymers, polyamides, polyesters, polyacetals, polycarbonates, polyurethanes, and copolymers, and mixtures thereof. The polymer layer typically consists of one or more polyurethanes.

An advantage of the sensor according to the present invention is that the sensitivity and dynamic range of the sensor can be adjusted by varying the density of nanoparticles in the layer and by varying the amount of recognizing component and/or transducer in each nanoparticle. Thus, for example, by having a high density of nanoparticles in the layer, fast sensor responses can be achieved.

In accordance with still yet another specific embodiment of the present invention, a sensor is provided comprising (a) a light-transmissive substrate, (b) a polymer layer having recognizing and optical transducer properties, wherein these properties are provided by a recognizing component and an optical transducer contained in the polymer layer deposited on (a), and (c) a membrane layer on top of the polymer layer.

The light-transmissive substrate in this embodiment of the present invention should be transmissive to radiation for exciting the optical transducer, which typically is a luminescent dye. Additionally, the radiation emitted from the transducer must pass the light-transmissive substrate in the opposite direction for detection. Typically, the light-transmissive substrate should have a low permeability to gas, in particular, oxygen. In particular, when using a transducer which is sensitive to gas (e.g., oxygen-sensitive), distortion of the response of the transducer can be avoided thereby. Suitable materials for the light-transmissive substrate are organic or inorganic materials, in particular polymeric materials, e.g., glass, in particular, MYLAR™ glass, polyethylene terephthalate (PET), and polyvinylidene chloride (PVO).

On this layer, a polymer layer as described above is deposited and the membrane layer (c) covers the polymer layer.

The membrane layer typically provides optical isolation and is coated on the polymer layer for adjustment of diffusional processes. It can be constructed such that only certain substances can pass, for example, the analyte to be detected, and typically is rapidly hydratable.

Possible materials for the membrane layer are non-water soluble polymers—typically polyurethane, polyacrylamide, polystyrene, polyvinyl esters and co-polymers of, e.g., butadiene and styrene. Typically, carbon black is incorporated in the membrane layer for optical isolation.

In accordance with yet still another embodiment of the present invention, a sensor for the detection of glucose in a sample is provided. In this embodiment, the recognizing component is the oxidative enzyme glucose oxidase and the optical transducer is a luminescent dye. Glucose present in the sample is oxidized by glucose oxidase and oxygen, consuming oxygen in the polymer layer. The transducer consisting of a luminescent dye which is oxygen-sensitive responds to the depletion of oxygen by increasing the luminescence intensity which can be detected spectroscopically.

A further advantage of the sensor according to the present invention is that it can be fast regenerated. For example, if used as an oxidative enzyme-based sensor, the oxygen concentration inside the polymer layer of the sensor, which was consumed during the enzymatic reaction with the target analyte, can be fast regenerated.

In accordance with still yet another embodiment of the present invention, a sensor which is suitable for the detection of analytes which cannot be enzymatically oxidized in a single step such as creatinine is provided. In this case, the recognizing component consists of several enzymes and creatinine is converted into an oxidizable intermediate (sarcosine) by a first enzyme, which then can be oxidized by an oxidative enzyme (sarcosine oxidase). The consumption of oxygen in the enzymatic oxidation can be detected by an oxygen-sensitive dye, analogous to the glucose sensor described above.

The sensor according to the present invention is very useful for qualitatively or quantitatively analyzing a sample such as a body liquid sample. Consequently, in accordance with a further embodiment of the present invention, the use of a sensor according to the invention for detecting and/or quantifying a target analyte is provided. For example, the sensor according to the present invention can be used for the detection of a specific substance in environmental, food, waste water, drinking water and medicinal samples, or for analysis in the field of biotechnology. The inventive sensor is particularly useful for medicinal applications such as, for example, the detection and/or quantification of target analytes in body liquid samples such as blood or serum, urine, and saliva in pure or diluted form. In particular, the target analyte of interest can be selected from the group consisting of glucose, lactate, sarcosine, creatinine and mixtures thereof, the sensor being particularly useful for detecting and/or quantifying glucose.

In accordance with a further embodiment of the present invention, a polymer layer having recognizing and transducer properties is provided, wherein these properties are provided by a recognizing component and a transducer contained in one or more nanoparticles embedded in the polymer layer.

Specific examples of suitable polymeric materials, transducers and recognizing components are given above.

The polymer layer is particularly useful for incorporation in a sensor as described above.

In accordance with yet still another embodiment of the present invention, a process for the production of a sensor comprising a polymer layer with recognizing and transducer properties is provided, the process comprising the steps of: (a) providing a light-transmissive substrate, (b) depositing on the substrate a polymer layer having recognizing and transducer properties, wherein these properties are provided by a recognizing component and a transducer contained in one or more nanoparticles embedded in the polymer layer, and (c) coating a membrane layer on top of the polymer layer.

Typically, the polymer layer according to step (b) is coated with a membrane layer incorporating carbon black (step (c)). This coating provides optical isolation and adjustment of diffusional processes.

In accordance with yet still another embodiment of the present invention, the use of a nanoparticle comprising a recognizing component and/or a transducer in a sensor or a polymer layer according to the invention is provided.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

In order that the invention may be more readily understood, reference is made to the following examples, which are intended to illustrate the invention, but not to limit the scope thereof.

EXAMPLE 1

Figure 1:
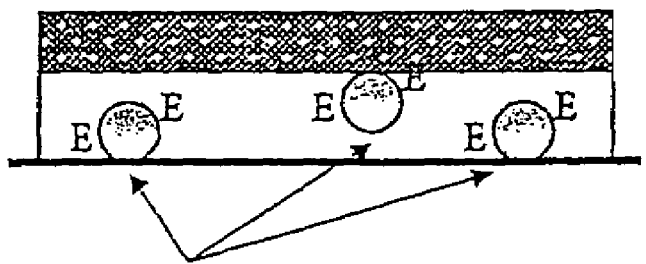
FIG. 1 is a schematic drawing illustrating two typical embodiments of the present invention. (A) represents the inventive polymer layer comprising nanoparticles doped with a luminescent dye and conjugated with an oxidative enzyme. (B) represents an embodiment of the invention, where two populations of nanoparticles are embedded in the polymer layer, nanoparticles doped with a luminescent dye, and nanoparticles conjugated with an oxidative enzyme.
Figure 1:
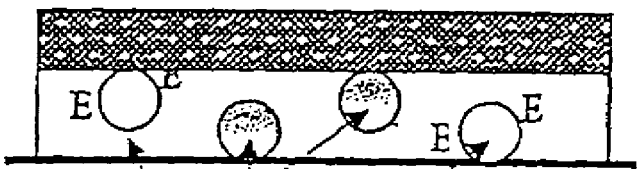
Figure 2:
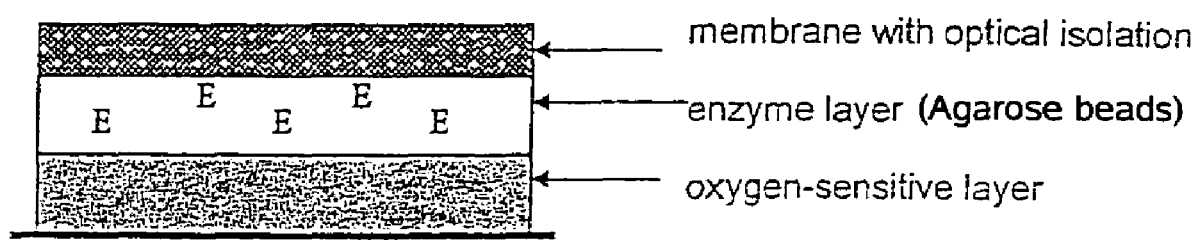
FIG. 2 shows a conventional multilayer-structured sensor, wherein the recognizing component (enzyme) and the transducer (oxygen-sensitive) are contained in separate layers.

A glucose sensor is constructed according to FIG. 1B and contains 30 mg of poly(tert-butylstyrene) nanoparticles doped with a ruthenium complex [Ru(diphenylphenanthroline)$_3$] and 50 mg of polystyrene nanoparticles conjugated with glucose oxidase dispersed in a polyurethane matrix.

On top of this multifunctional layer, a membrane incorporating carbon black is then coated for optical isolation and for the adjustment of diffusional processes.

The Table below illustrates the fluorescence signal response [kinetic measurements: fluorescence intensity change per second (Äl per second)] to various levels of glucose in control solutions tonometered at 150 Torr oxygen partial pressure.

| Glucose Concentration (mg/dL) | Relative Slope (Äl per second) |
| --- | --- |
| 50 | 727 |
| 113 | 1451 |
| 356 | 3752 |

After injection of each control solution the cassette was washed manually 5 times with the Opti buffer tonometered at 90 Torr of oxygen before being flushed externally with a gas containing 90 Torr oxygen for the recalibration (recalibration times were less than 60 s).

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A sensor comprising a polymer layer, said polymer layer comprising recognizing and transducing properties, wherein
said recognizing properties are provided by a recognizing component,
said transducing properties are provided by a transducer, and
said recognizing component and said transducer are contained in one or more solid or semi-solid nanoparticles, wherein said nanoparticles have a mean diameter of between about 10 and 500 nm and wherein said nanoparticles are embedded in said polymer layer.

2. The sensor of claim 1, wherein said nanoparticles further comprise first or second nanoparticles, and wherein
said first nanoparticles comprise said recognizing component, and
said second nanoparticles comprise said transducer.

3. The sensor of claim 1, wherein said nanoparticles embedded in said polymer layer comprise both recognizing component and said transducer.

4. The sensor of claim 1, wherein said recognizing component comprises a bioactive component.

5. The sensor of claim 4, wherein said bioactive component comprises an enzyme.

6. The sensor of claim 5, wherein said enzyme is selected from the group consisting of synthetic enzymes and gene-manipulated enzymes.

7. The sensor of claim 5, wherein said enzyme comprises an oxidative enzyme.

8. The sensor of claim 7, wherein said oxidative enzyme is selected from the group consisting of glucose oxidase, cholesterol oxidase, lactate oxidase, sarcosine oxidase, and mixtures thereof.

9. The sensor of claim 7, wherein the oxidase enzyme comprises glucose oxidase.

10. The sensor of claim 1, wherein said transducer comprises an optical transducer.

11. The sensor of claim 10, wherein said optical transducer comprises a luminescent dye.

12. The sensor of claim 11, wherein said luminescent dye is selected from the group consisting of [Ru(diphenylphenantroline)$_3$], octaethyl-Pt-porphyrin, octaethyl-Pt-porphyrin ketone, tetrabenzo-Pt-porphyrin, tetraphenyl-Pt-porphyrin, meso-tetraphenyl-tetrabenzo-Pt-porphyrin, tetracylcohexenyl-Pt-porphyrin, octaethyl-Pt-chlorine, tetraphenyl-Pt-chlorine, and mixtures thereof.

13. The sensor of claim 1, wherein said nanoparticles comprise a polymer material.

14. The sensor of claim 13, wherein said polymer material is selected from the group consisting of polyolefins, vinyl polymers, polyamides, polyesters, polyacetals, polycarbonates, polyurethanes, polysiloxanes, copolymers, and mixtures thereof.

15. The sensor of claim 1, wherein said polymer layers comprises a polymer selected from the group consisting of polyolefins, vinyl polymers, polyamides, polyesters, polyacetals, polycarbonates, polyurethanes, polysiloxanes, copolymers, and mixtures thereof.

16. The sensor of claim 1, wherein said polymer layers comprises one or more polyurethanes.

17. The sensor of claim 1, wherein said recognizing component and said transducer are entrapped within, conjugated to, or attached to one or more said nanoparticles embedded in said polymer layer.

18. The sensor of claim 1, wherein said sensor is used for detecting and/or quantifying a target analyte.

19. The sensor of claim 18, wherein said target analyte is selected from the group consisting of glucose, lactate, sarcosine, creatine, and mixtures thereof.

20. The sensor of claim 18, wherein said target analyte is glucose.

21. The sensor of claim 18, wherein said target analyte is contained within a body liquid sample.

22. A sensor comprising:
a light-transmissive substrate;
a polymer layer comprising recognizing and optical transducing properties wherein
said recognizing properties are provided by a recognizing component,
said optical transducing properties are provided by an optical transducer,
said recognizing component and said optical transducer are contained in one or more solid or semi-solid nanoparticles, wherein said nanoparticles have a mean diameter of between 10 and about 500 nm,
said nanoparticles are embedded in said polymer layer, and
said polymer layer is deposited on said light-transmissive substrate, and
a membrane layer positioned on top of said polymer layer.

* * * * *